United States Patent
Leppert et al.

(10) Patent No.: US 8,809,316 B2
(45) Date of Patent: Aug. 19, 2014

(54) USE OF IMMUNOSUPPRESSANT COMPOUNDS IN A NEW INDICATION

(71) Applicants: David Leppert, Oberwil (CH); Erik Wallstroem, Binningen (CH); Barbara Nuesslein-Hildesheim, Eimeldigen (DE)

(72) Inventors: David Leppert, Oberwil (CH); Erik Wallstroem, Binningen (CH); Barbara Nuesslein-Hildesheim, Eimeldigen (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/787,423

(22) Filed: Mar. 6, 2013

(65) Prior Publication Data

US 2014/0011797 A1 Jan. 9, 2014

Related U.S. Application Data

(63) Continuation of application No. 13/059,346, filed as application No. PCT/EP2009/060611 on Aug. 17, 2009, now abandoned.

(30) Foreign Application Priority Data

Aug. 18, 2008 (EP) .................................. 08162517

(51) Int. Cl.
*A61K 31/397* (2006.01)
*C07D 205/04* (2006.01)

(52) U.S. Cl.
CPC ................. *A61K 31/397* (2013.01); *C07D 205/04* (2013.01)
USPC .................................................... 514/210.17

(58) Field of Classification Search
CPC ............................ A61K 31/397; C07D 205/04
USPC .................................................... 514/210.17
See application file for complete search history.

(56) References Cited

U.S. PATENT DOCUMENTS

2005/0014728 A1 * 1/2005 Pan et al. ...................... 514/114
2010/0310547 A1 * 12/2010 Soliven ...................... 424/130.1

FOREIGN PATENT DOCUMENTS

| WO | WO 2004/103306 A | 12/2004 | |
| WO | 2006058316 | 6/2006 | |
| WO | WO 2008/000419 A | 1/2008 | |
| WO | WO 2008/021532 | * 2/2008 | .......... A61K 31/133 |
| WO | 2009048993 A2 | 4/2009 | |
| WO | 2010010127 A1 | 1/2010 | |

OTHER PUBLICATIONS

Aguilar et al. (Bioorg. Med. Chem. Lett. 22 (2012) 7672-7676).*
Enders et al. (Journal of Neuroimmunology 76 1997 112-116).*
Wermuth, The Practice of Medicinal Chemsitry, 2d ed. (2003), 768 pages. Chs. 9-10 provided.*
Brinkmann (Pharmacology & Therapeutics 115 (2007) 84-105).*
M.Д. Машkobckий, "Лekapctbehhble cpeд ctba," Mockba, "Me дичиha", 1993, 4.1, c.8 (in Russian Only) M.D. Mashkovskij, "Lekarstvennye sredstva," Moskva, "Medicina", 1993, ch.1, s.8).
Химический зh чи knoneдиче ский cnobapb, Mockba, "Cobetckaя Зhчиknoneдия, 1983, c. 130-131(in Russian only) Himicheskij jenciklopedicheskij slovar", Moskva, Sovetskaja jenciklopedija, 1983, s. 130-131.
M.D. Mashkovskij, "Medicinal Drugs," Moscow, t.1, 2001, s.11.

* cited by examiner

*Primary Examiner* — Robert Havlin
(74) *Attorney, Agent, or Firm* — Jim Lynch

(57) ABSTRACT

The present invention discloses various immunosuppressants, salts and polymorphs thereof useful in the treatment of various disorders, including peripheral neuropathy. The invention also discloses pharmaceutical formulations utilizing the immunosuppressants, alone or in combination with other compounds, useful in treating disorders such as peripheral neuropathy. The present invention also discloses a method of treating peripheral neuropathy with immunosuppressants disclosed herein.

3 Claims, 2 Drawing Sheets

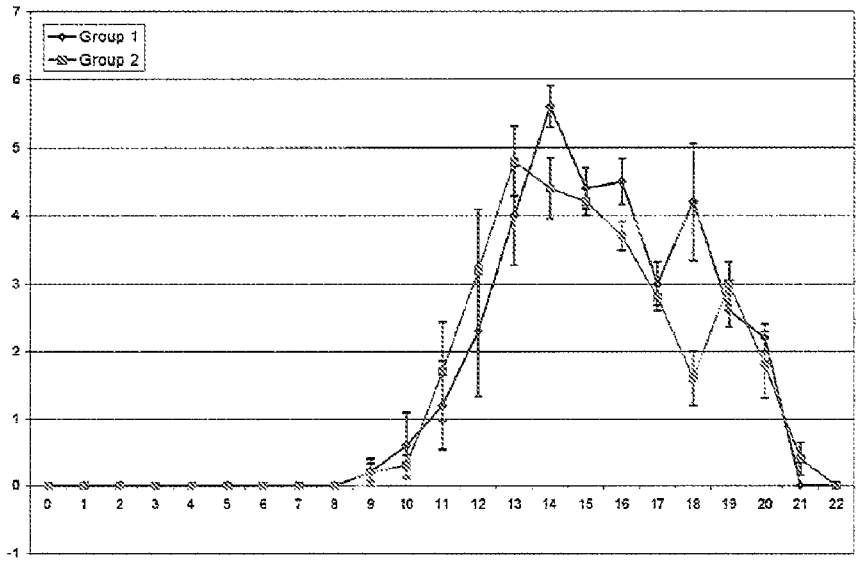
Figure 1A – Neurological score vs no. of days after immunisation for EAN rats treated with water vehicle (group 1) and CMC vehicle (group 2).
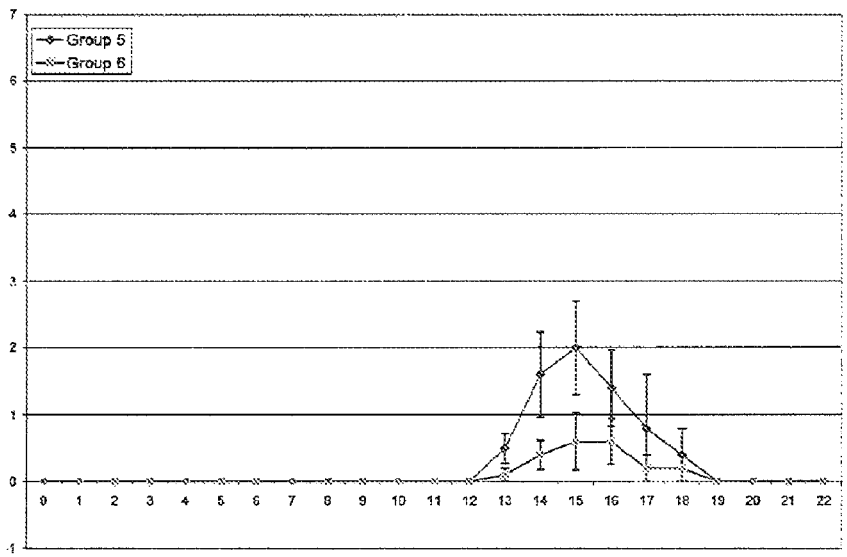
Figure 1B - Neurological score vs no. of days after immunisation for EAN rats treated with 3mg/kg compound A suspension (group 5) and 10 mg/kg compound A suspension (group 6).

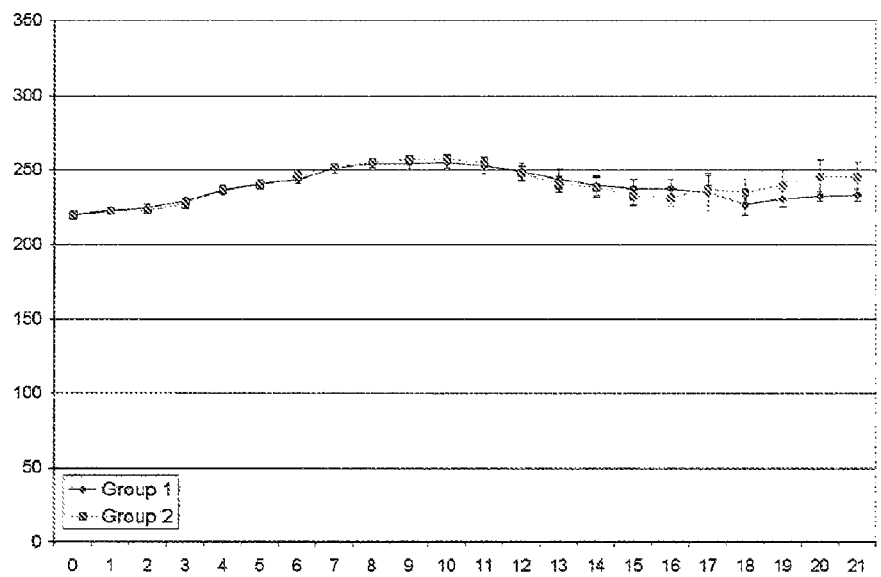
Figure 2A – Weight vs no. of days after immunisation for EAN rats treated with water vehicle (group 1) and CMC vehicle (group 2).
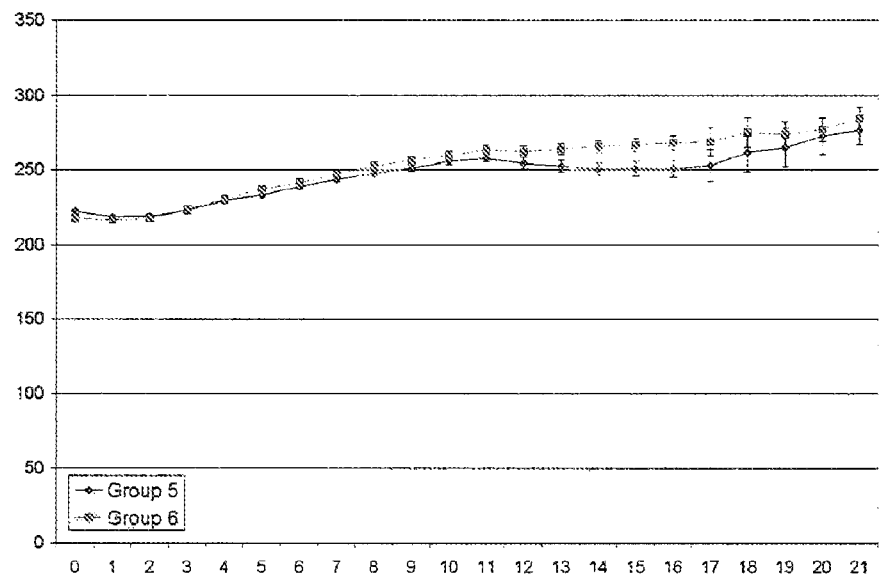
Figure 2B - Weight vs no. of days after immunisation for EAN rats treated with 3mg/kg compound A suspension (group 5) and 10 mg/kg compound A suspension (group 6).

USE OF IMMUNOSUPPRESSANT COMPOUNDS IN A NEW INDICATION

FIELD OF THE INVENTION

The present invention relates to immunosuppressant compounds and their use in therapy.

BACKGROUND TO THE INVENTION

The inflammatory or immune-mediated neuropathies are a diverse group of diseases which include such peripheral neuropathies as Guillain-Barré syndrome (GBS), chronic inflammatory demyelinating polyradiculoneuropathy (CIDP), multifocal motor neuropathy with conduction block (MMN), and paraproteinaemic demyelinating peripheral neuropathy (PDN). The pathogenesis of the inflammatory neuropathies is still under investigation.

A number of demyelinating peripheral neuropathies are next discussed.

Peripheral neuropathies, therefore, include Guillain-Barré syndrome, which is an acute, autoimmune, polyneuropathy affecting the peripheral nervous system, usually triggered by an acute infectious process. There are several types of GBS, the most common form being acute inflammatory demyelinating polyneuropathy (AIDP). GBS is frequently severe and usually exhibits as an ascending paralysis noted by weakness in the legs that spreads to the upper limbs and the face along with complete loss of deep tendon reflexes. The suppressor T cell response is reduced suggesting a cell-mediated immunological reaction directed at the peripheral nerves.

Multifocal motor neuropathy is a progressive muscle disorder characterized by muscle weakness in the hands, with differences from one side of the body to the other in the specific muscles involved. Symptoms also include muscle wasting, cramping, and involuntary contractions or twitching of the leg muscles. Multifocal motor neuropathy is recognized to be an immune-mediated disorder.

Paraproteinaemic Demyelinating Neuropathy is a major cause of late onset demyelinating neuropathy, very similar to CIDP though more chronic. It mostly affects people of 60 years and over. Patients have many symptoms to contend with and it tends to be a long-term illness Chronic inflammatory demyelinating polyneuropathy (CIDP) is characterised by progressive weakness and impaired sensory function in the legs and arms. These symptoms are caused by damage to the myelin sheath of the peripheral nerves. It often presents with symptoms that include tingling or numbness (beginning in the toes and fingers), weakness of the arms and legs, loss of deep tendon reflexes, fatigue, and abnormal sensations. The prevalence of CIDP is about 2 to 4 per 100,000. The pathogenesis is uncertain but may involve both T and B cell-mediated mechanisms.

The course of CIDP varies widely among individuals. Some may have a bout of CIDP followed by spontaneous recovery, while others may have many bouts with partial recovery in between relapses. CIDP leads to severe disability in a considerable number of patients. Current treatments are aimed at modulating the immune response to achieve remission and maintain functional status.

WO 2004/103306 and US 2005/0014728 describe compounds useful in the treatment of diseases or disorders mediated by lymphocyte interactions. The aforesaid publications are incorporated herein by reference in their entirety for all purposes, in particular the following parts of US 2005/0014728: paragraphs [0006] to [0015], [0022] to [0042], [0102] to [0124] and [0126] to [0149] and Table 1. Particularly to be mentioned are Examples 1 to 5 of US 2005/0014728.

SUMMARY OF THE INVENTION

In one aspect of the invention there are provided compounds as mentioned below for use in the treatment of a peripheral neuropathy, e.g. CIDP. Another aspect of the invention resides in a method of treating a subject having a peripheral neuropathy, e.g. CIDP, comprising administering to the subject an effective amount of a compound as mentioned below. A further aspect of the invention is the use of a compound as mentioned below for the manufacture of a medicament for use in treating a peripheral neuropathy, e.g. CIDP.

The compounds to which the application relates are compounds as disclosed in WO 04/103306 and US 2005/0014728, WO 05/000833, WO 05/103309 or WO 05/113330, e.g. compounds of formula A1 or A2

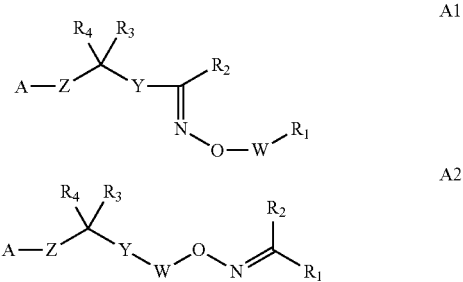

wherein

A is $COOR_5$, $OPO(OR_5)_2$, $PO(OR_5)_2$, $SO_2OR_5$, $POR_5OR_5$ or 1H-tetrazol-5-yl, $R_5$ being H or an ester-forming group, e.g. $C_{1-6}$alkyl;

W is a bond, $C_{1-3}$alkylene or $C_{2-3}$alkenylene;

Y is $C_{6-10}$aryl or $C_{2-9}$heteroaryl eg $C_{3-9}$heteroaryl, optionally substituted by 1 to 3 radicals selected from halogen, OH, $NO_2$, $C_{1-6}$alkyl, $C_{1-6}$alkoxy; halo-substituted $C_{1-6}$alkyl and halo-substituted $C_{1-6}$alkoxy;

Z is chosen from:

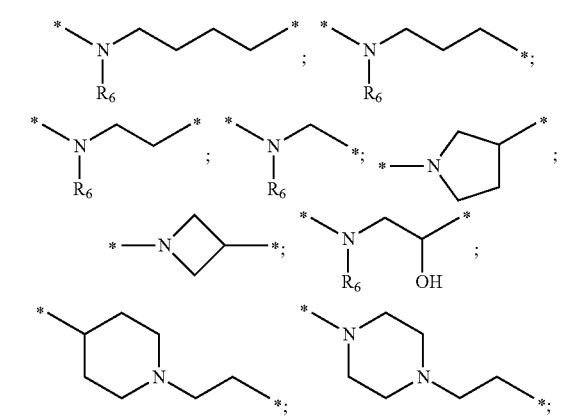

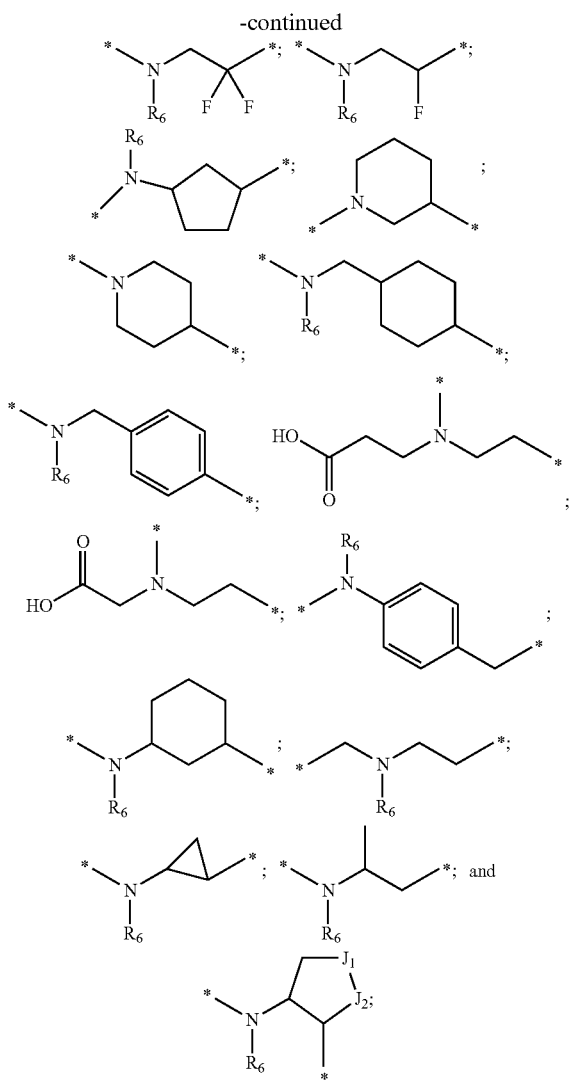

wherein the left and right asterisks of Z indicate the point of attachment between —C(R$_3$)(R$_4$)— and A of Formula Ia or Ib, respectively; R$_6$ is chosen from hydrogen and C$_{1-6}$alkyl; and J$_1$ and J$_2$ are independently methylene or a heteroatom chosen from S, O and NR$_5$; wherein R$_5$ is chosen from hydrogen and C$_{1-6}$alkyl; and any alkylene of Z can be further substituted by one to three radicals chosen from halo, hydroxy, C$_{1-6}$alkyl; or R$_6$ can be attached to a carbon atom of Y to form a 5-7 member ring;

R$_1$ is C$_{6-10}$aryl or C$_{2-9}$heteroaryl eg C$_{3-9}$heteroaryl, optionally substituted by C$_{1-6}$alkyl, C$_{6-10}$aryl, C$_{6-10}$arylC$_{1-4}$alkyl, C$_{3-9}$heteroaryl, C$_{3-9}$heteroarylC$_{1-4}$alkyl, C$_{3-8}$cycloalkyl, C$_{3-8}$cycloalkylC$_{1-4}$alkyl, C$_{3-8}$heterocycloalkyl or C$_{3-8}$heterocycloalkylC$_{1-4}$alkyl; wherein any aryl, heteroaryl, cycloalkyl or heterocycloalkyl of R$_1$ may be substituted by 1 to 5 groups selected from halogen, C$_{1-6}$alkyl, C$_{1-6}$alkoxy and halo substituted-C$_{1-6}$alkyl or —C$_{1-6}$alkoxy;

R$_2$ is H, C$_{1-6}$alkyl, halo substituted C$_{1-6}$alkyl, C$_{2-6}$alkenyl or C$_{2-6}$alkynyl; and each of R$_3$ or R$_4$, independently, is H, halogen, OH, C$_{1-6}$alkyl, C$_{1-6}$alkoxy or halo substituted C$_{1-6}$alkyl or C$_{1-6}$alkoxy;

and the N-oxide derivatives thereof or prodrugs thereof, or a pharmacologically acceptable salt, solvate or hydrate thereof.

Also provided are pharmaceutical formulations for use in treating a peripheral neuropathy, e.g. CIDP and comprising a compound of the disclosure and, optionally, a pharmaceutically acceptable diluent or carrier. In embodiments, the pharmaceutical formulations contain one or more additional therapeutic agents.

The invention also provides a product comprising a compound of the disclosure and a therapeutic agent as a combined preparation for simultaneous, separate or sequential use in treating a peripheral neuropathy, e.g. CIDP.

In another aspect, the invention provides a pharmaceutical formulation comprising a compound of the disclosure and a therapeutic agent, the therapeutic agent being useful for the treatment of a peripheral neuropathy, e.g. CIDP.

The compounds of the invention can exist in different forms, such as free acids, free bases, esters and other prodrugs, salts and tautomers, for example, and the disclosure includes all variant forms of the compounds.

The extent of protection includes counterfeit or fraudulent products which contain or purport to contain a compound of the invention irrespective of whether they do in fact contain such a compound and irrespective of whether any such compound is contained in a therapeutically effective amount.

Included in the scope of protection are packages which include a description or instructions which indicate that the package contains a species or pharmaceutical formulation of the invention and a product which is or comprises, or purports to be or comprise, such a formulation or species. Such packages may be, but are not necessarily, counterfeit or fraudulent.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE FIGURES

FIG. 1A shows the variation of neurological score with no. of days from immunisation for EAN rats treated with water vehicle and CMC vehicle.

FIG. 1B shows the variation of neurological score with no. of days from immunisation for EAN rats treated with 3 and 10 mg/kg concentration compound A suspensions.

FIG. 2A shows the variation in body weight with no. of days from immunisation for EAN rats treated with water vehicle and CMC vehicle.

FIG. 2B shows the variation in body weight with no. of days from immunisation for EAN rats treated with 3 and 10 mg/kg concentration compound A suspensions.

DESCRIPTION OF VARIOUS EMBODIMENTS

Definitions

In this specification, unless otherwise defined:

Alkyl, Alkenyl, Alkynyl

"Alkyl" as a group and as a structural element of other groups, for example halo-substituted-alkyl, alkoxy, acyl, alkylthio, alkylsulfonyl and alkylsulfinyl, can be either straight-chained or branched, and unless otherwise indicated may have from 1 to 6 carbon atoms. A C$_1$-C$_6$ alkyl moiety may have 1, 2, 3, 4, 5 or 6 carbon atoms. "Alkenyl" as a group and as a structural element of other groups contains one or more carbon-carbon double bonds, and can be either straight-chain, or branched. Double bonds can be in the cis- or trans-configuration. "Alkynyl" as a group and as structural element of other groups and compounds contains at least one C≡C triple bond and can also contain one or more C═C double bonds, and can, so far as possible, be either straight-chain or branched. Unless otherwise indicated, alkenyl and alkynyl residues may have 2, 3, 4, 5 or 6 carbon atoms. Any cycloalkyl group, alone or as a structural element of other groups, can contain 3, 4, 5, 6, 7 or 8 carbon atoms, preferably 3, 4, 5 or 6 carbon atoms. "Alkylene" and "alkenylene" are divalent radicals derived from "alkyl" and "alkenyl" groups, respectively. In this application, any alkyl group of $R_1$ is optionally an interrupted alkyl group which has a methylene replaced by a member of the group selected from —S—, —S(O)—, —S(O)$_2$—, —NR$^{20}$— and —O— (wherein R$^{20}$ is hydrogen or $C_{1-6}$alkyl). These groups include, for example, —CH$_2$—O—CH$_2$—, —CH$_2$—S(O)$_2$—CH$_2$—, —(CH$_2$)$_2$—NR$^{20}$—CH$_2$, —CH$_2$—O—(CH$_2$)$_2$—. In one embodiment, there are no such interrupted alkyl groups; included thereof is a class of compounds in which all alkyl groups are uninterrupted.

Aryl

"Aryl" means a monocyclic or fused bicyclic aromatic ring assembly containing six to ten ring carbon atoms. For example, $C_{6-10}$aryl can be phenyl, biphenyl or naphthyl, preferably phenyl. A fused bicyclic ring can be partially saturated, for example, 1,2,3,4-tetrahydro-naphthalene, and the like. "Arylene" means a divalent radical derived from an aryl group. For example, arylene as used in this application can be phenylene, biphenylene, naphthylene and the like.

Halogen

"Halo" or "halogen" means F, Cl, Br or I, preferably F or Cl. Halo-substituted alkyl groups and compounds can be partially halogenated or perhalogenated, whereby in the case of multiple halogenation, the halogen substituents can be identical or different. A preferred perhalogenated alkyl group is for example trifluoromethyl or trifluoromethoxy.

Heteroaryl

"Heteroaryl" means aryl, as defined in this application, with the inclusion in the ring structure of at least one heteroatom moiety selected from N, O or S, and each ring is comprised of 5 to 6 ring atoms, unless otherwise stated. For example, $C_2$heteroaryl includes oxadiazole, triazole, and the like. $C_9$heteroaryl includes quinoline, 1,2,3,4-tetrahydro-quinoline, and the like. $C_{2-9}$heteroaryl as used in this application includes thienyl, pyridinyl, furanyl, isoxazolyl, benzoxazolyl or benzo[1,3]dioxolyl, preferably thienyl, furanyl or pyridinyl. "Heteroarylene" means heteroaryl, as defined in this application, provided that the ring assembly comprises a divalent radical. A fused bicyclic heteroaryl ring system can be partially saturated, for example, 2,3-dihydro-1H-isoindole, 1,2,3,4-tetrahydro-quinoline, and the like.

Substituted

Unless otherwise indicated, the term "substituted" as used herein in reference to a moiety means that one or more, especially up to 5, more especially 1, 2 or 3, of the hydrogen atoms in said moiety are replaced independently of each other by the corresponding number of the described substituents. The term "optionally substituted" as used herein means substituted or unsubstituted.

It will, of course, be understood that substituents are only at positions where they are chemically possible, the person skilled in the art being able to decide (either experimentally or theoretically) without inappropriate effort whether a particular substitution is possible. For example, amino or hydroxy groups with free hydrogen may be unstable if bound to carbon atoms with unsaturated (e.g. olefinic) bonds.

Pharmaceutically Acceptable

The term "pharmaceutically acceptable" as used herein includes reference to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio. This term includes acceptability for both human and veterinary purposes.

Independently

Where two or more moieties are described as being "each independently" selected from a list of atoms or groups, this means that the moieties may be the same or different. The identity of each moiety is therefore independent of the identities of the one or more other moieties.

Compounds

The application relates to compounds as disclosed in WO 2004/103306 and US 2005/0014728, WO 05/000833, WO 05/103309 or WO 05/113330, e.g. compounds of formula A1 or A2

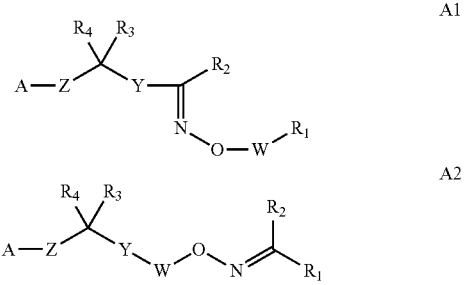

wherein

A is COOR$_5$, OPO(OR$_5$)$_2$, PO(OR$_5$)$_2$, SO$_2$OR$_5$, POR$_5$OR$_5$ or 1H-tetrazol-5-yl, R$_5$ being H or an ester-forming group, e.g. $C_{1-6}$alkyl;

W is a bond, $C_{1-3}$alkylene or $C_{2-3}$alkenylene;

Y is $C_{6-10}$aryl or $C_{2-9}$heteroaryl eg $C_{3-9}$heteroaryl, optionally substituted by 1 to 3 radicals selected from halogen, OH, NO$_2$, $C_{1-6}$alkyl, $C_{1-6}$alkoxy; halo-substituted $C_{1-6}$alkyl and halo-substituted $C_{1-6}$alkoxy;

Z is chosen from:

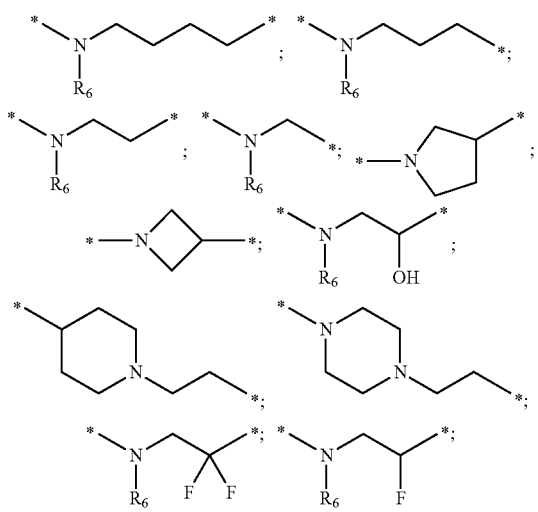

-continued

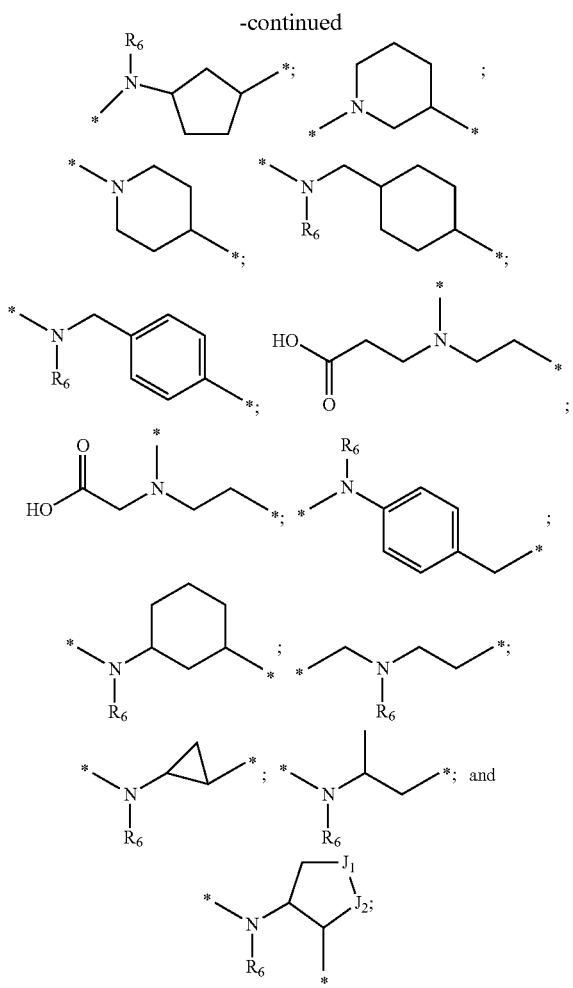

wherein the asterisks of Z indicate the point of attachment between —C(R$_3$)(R$_4$)— and A of Formula Ia or Ib, respectively; R$_6$ is chosen from hydrogen and C$_{1-6}$alkyl; and J$_1$ and J$_2$ are independently methylene or a heteroatom chosen from S, O and NR$_5$; wherein R$_5$ is chosen from hydrogen and C$_{1-6}$alkyl; and any alkylene of Z can be further substituted by one to three radicals chosen from halo, hydroxy, C$_{1-6}$alkyl; or R$_6$ can be attached to a carbon atom of Y to form a 5-7 member ring;

R$_1$ is C$_{6-10}$aryl or C$_{2-9}$heteroaryl eg C$_{3-9}$heteroaryl, optionally substituted by C$_{1-6}$alkyl, C$_{6-10}$aryl, C$_{6-10}$arylC$_{1-4}$alkyl, C$_{3-9}$heteroaryl, C$_{3-9}$heteroarylC$_{1-4}$alkyl, C$_{3-8}$cycloalkyl, C$_{3-8}$cycloalkylC$_{1-4}$alkyl, C$_{3-8}$heterocycloalkyl or C$_{3-8}$heterocycloalkylC$_{1-4}$alkyl; wherein any aryl, heteroaryl, cycloalkyl or heterocycloalkyl of R$_1$ may be substituted by 1 to 5 groups selected from halogen, C$_{1-6}$alkyl, C$_{1-6}$alkoxy and halo substituted-C$_{1-6}$alkyl or —C$_{1-6}$alkoxy;

R$_2$ is H, C$_{1-6}$alkyl, halo substituted C$_{1-6}$alkyl, C$_{2-6}$alkenyl or C$_{2-6}$alkyny; and each of R$_3$ or R$_4$, independently, is H, halogen, OH, C$_{1-6}$alkyl, C$_{1-6}$alkoxy or halo substituted C$_{1-6}$alkyl or C$_{1-6}$alkoxy;

and the N-oxide derivatives thereof or prodrugs thereof, or a pharmacologically acceptable salt, solvate or hydrate thereof.

Further embodiments of the invention are described below. It will be appreciated that the features specified in each embodiment may be combined with other specified features, to provide further embodiments.

A is COOR$_5$, OPO(OR$_5$)$_2$, PO(OR$_5$)$_2$, SO$_2$OR$_5$, POR$_5$OR$_5$ or 1H-tetrazol-5-yl, R$_5$ being H or an ester-forming group, e.g. C$_{1-6}$alkyl. A is in particular COOR$_5$, e.g. COOH.

W is a bond, C$_1$, C$_2$ or C$_3$alkylene or C$_{2-3}$alkenylene. In embodiments, W is ethylene.

Y is C$_{6-10}$aryl or C$_{2-9}$heteroaryl eg C$_{3-9}$heteroaryl, optionally substituted by 1 to 3 radicals selected from halogen, OH, NO$_2$, alkyl, alkoxy; halo-substituted alkyl and halo-substituted alkoxy, wherein alkyl as a group or as part of alkoxy, whether or not halo-substituted, has 1, 2, 3, 4, 5 or 6 carbon atoms. Y is in particular phenyl or C$_6$heteroaryl, in either case optionally substituted as aforesaid. Said aryl, e.g. phenyl, or heteroaryl group may have one substituent, for example a single said alkyl substituent. An exemplary alkyl substituent is ethyl. Halogen is in particular F or Cl.

Z is a moiety as mentioned above, particularly a heterocyclic group as indicated in WO 2004/103306, e.g. azetidine, particularly azetidine joined to the remainder of the molecule at the 1- and 3-positions. Also to be mentioned are: pyrrolidine and piperidine, in either case joined to the remainder of the molecule at the 1- and 3-positions; and piperidine 1,4-disubstituted by the respective moieties forming the remainder of the molecule. These heterocycles are in some compounds N-substituted (1-substituted) by moiety A and substituted at the 3- or, as the case may be, 4-position by CR$_3$R$_4$.

R$_1$ is C$_{6-10}$aryl or C$_{2-9}$heteroaryl eg C$_{3-9}$heteroaryl, optionally substituted by C$_{1-6}$alkyl, C$_{6-10}$aryl, C$_{6-10}$arylC$_{1-4}$alkyl, C$_{3-9}$heteroaryl, C$_{3-9}$heteroarylC$_{1-4}$alkyl, C$_{3-8}$cycloalkyl, C$_{3-8}$cycloalkylC$_{1-4}$alkyl, C$_{3-8}$heterocycloalkyl or C$_{3-8}$heterocycloalkylC$_{1-4}$alkyl; wherein any aryl, heteroaryl, cycloalkyl or heterocycloalkyl of R$_1$ may be substituted by 1 to 5 groups selected from halogen, C$_{1-6}$alkyl, C$_{1-6}$alkoxy and halo substituted-C$_{1-6}$alkyl or —C$_{1-6}$alkoxy. R$_1$ is in particular phenyl or C$_6$heteroaryl optionally substituted as aforesaid. R$_1$ in some embodiments has two substituents selected from optionally halo-substituted alkyl having 1, 2, 3, 4, 5 or 6 carbon atoms (e.g. trifluoromethyl), optionally halo-substituted phenyl and optionally halo-substituted C$_{3-8}$cycloalkyl (e.g. cyclohexyl), for example R$_1$ may have one optionally halo-substituted alkyl group and one optionally halo-substituted cyclic moiety selected from phenyl and C$_{3-8}$ (e.g. C$_6$)cycloalkyl groups. R$_1$ is in some compounds phenyl or C$_6$heteroaryl, particularly phenyl, 3,4-disubstituted as aforesaid, as in the case of 3-trifluoromethyl-4-cyclohexylphenyl.

R$_2$ is H, C$_{1-6}$alkyl, halo substituted C$_{1-6}$alkyl, C$_{2-6}$alkenyl or C$_{2-6}$alkynyl. Alkyl, whether or not halo-substituted, may therefore have 1, 2, 3, 4, 5 or 6 carbon atoms. R$_2$ is in particular methyl.

Each of R$_3$ and R$_4$, independently, is H, halogen, OH, C$_{1-6}$alkyl, C$_{1-6}$alkoxy or halo substituted C$_{1-6}$alkyl or C$_{1-6}$alkoxy. Alkyl, whether or not halo-substituted and/or part of alkoxy, may therefore have 1, 2, 3, 4, 5 or 6 carbon atoms. R$_3$ and R$_4$ may by way of example each independently be H, halogen, methyl or halo-substituted methyl. In particular, R$_3$ and R$_4$ may both be H.

A preferred compound useful for the purposes of the invention is 1-{4-[1-(4-Cyclohexyl-3-trifluoromethyl-benzyloxy-imino)-ethyl]-2-ethyl-benzyl}-azetidine-3-carboxylic acid:

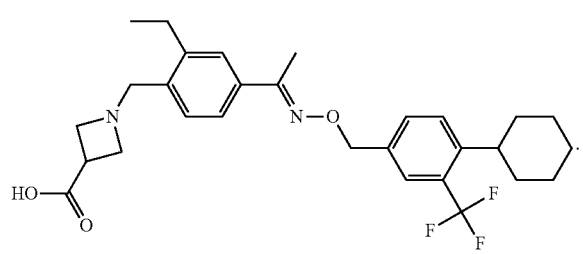 [SMILES: CCc1cc(/C(C)=N/OCc2ccc(C3CCCCC3)c(C(F)(F)F)c2)ccc1CN1CC(C(=O)O)C1]

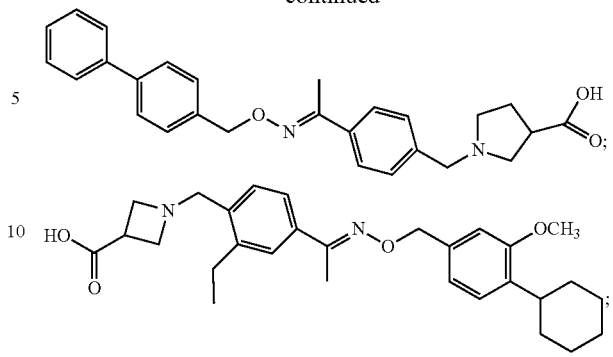

Further compounds useful for the purposes of the invention include:

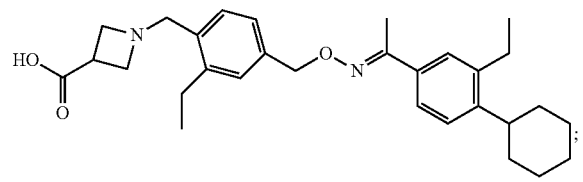

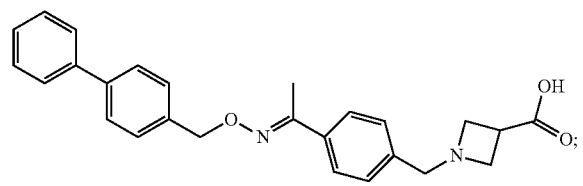

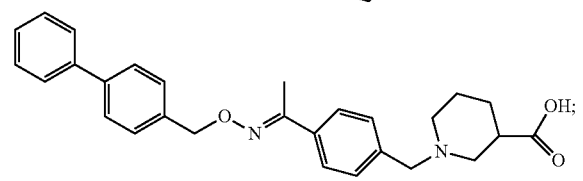

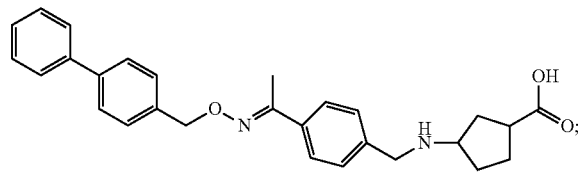

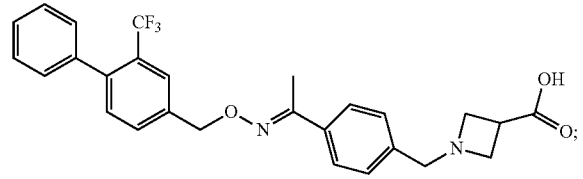

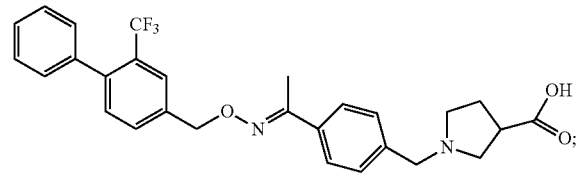

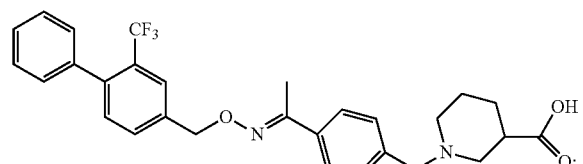

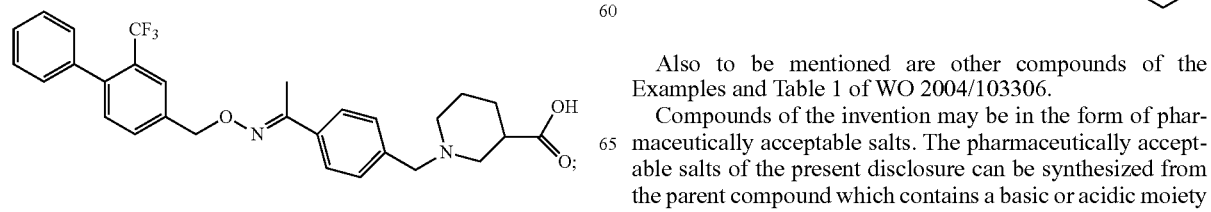

Also to be mentioned are other compounds of the Examples and Table 1 of WO 2004/103306.

Compounds of the invention may be in the form of pharmaceutically acceptable salts. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., US, 1985, p. 1418, the disclosure of which is hereby incorporated by reference; see also Stahl et al, Eds, "Handbook of Pharmaceutical Salts Properties Selection and Use", Verlag Helvetica Chimica Acta and Wiley-VCH, 2002.

The disclosure thus includes pharmaceutically-acceptable salts of the disclosed compounds wherein the parent compound is modified by making acid or base salts thereof. For example the conventional non-toxic salts or the quaternary ammonium salts which are formed, e.g. from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The invention includes prodrugs for the active pharmaceutical species of the invention, for example in which one or more functional groups are protected or derivatised but can be converted in vivo to the functional group, as in the case of esters of carboxylic acids convertible in vivo to the free acid, or in the case of protected amines, to the free amino group. The term "prodrug," as used herein, represents in particular compounds which are rapidly transformed in vivo to the parent compound, for example, by hydrolysis in blood. A thorough discussion is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987; H Bundgaard, ed, Design of Prodrugs, Elsevier, 1985; and Judkins, et al. Synthetic Communications, 26(23), 4351-4367 (1996), each of which is incorporated herein by reference.

Prodrugs therefore include drugs having a functional group which has been transformed into a reversible derivative thereof. Typically, such prodrugs are transformed to the active drug by hydrolysis. As examples may be mentioned the following:

| Functional Group | Reversible derivative |
|---|---|
| Carboxylic acid | Esters, including e.g. alkyl and acyloxyalkyl esters; amides |
| Alcohol | Esters, including e.g. sulfates and phosphates as well as carboxylic acid (e.g. alkanoic acid) esters |
| Amine | Amides, carbamates, imines, enamines, |
| Carbonyl (aldehyde, ketone) | Imines, oximes, acetals/ketals, enol esters, oxazolidines and thiazoxolidines |

Prodrugs also include compounds convertible to the active drug by an oxidative or reductive reaction. As examples may be mentioned:

Oxidative Activation
N- and O-dealkylation
Oxidative deamination
N-oxidation
Epoxidation
Reductive Activation
Azo reduction
Sulfoxide reduction
Disulfide reduction
Bioreductive alkylation
Nitro reduction.

Also to be mentioned as metabolic activations of prodrugs are nucleotide activation, phosphorylation activation and decarboxylation activation. For additional information, see "The Organic Chemistry of Drug Design and Drug Action", R B Silverman (particularly Chapter 8, pages 497 to 546), incorporated herein by reference.

The use of protecting groups is fully described in 'Protective Groups in Organic Chemistry', edited by J W F McOmie, Plenum Press (1973), and 'Protective Groups in Organic Synthesis', 2nd edition, T W Greene & P G M Wutz, Wiley-Interscience (1991).

Thus, it will be appreciated by those skilled in the art that, although protected derivatives of compounds of the disclosure may not possess pharmacological activity as such, they may be administered, for example parenterally or orally, and thereafter metabolised in the body to form compounds of the invention which are pharmacologically active. Such derivatives are therefore examples of "prodrugs". All prodrugs of the described compounds are included within the scope of the disclosure.

Some groups mentioned herein (especially those containing heteroatoms and conjugated bonds) may exist in tautomeric forms and all these tautomers are included in the scope of the disclosure. More generally, many species may exist in equilibrium, as for example in the case of organic acids and their counterpart anions; a reference herein to a species accordingly includes reference to all equilibrium forms thereof.

The compounds of the disclosure may also contain one or more asymmetric carbon atoms and may therefore exhibit optical and/or diastereoisomerism. All diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric derivatives by conventional means (e.g. HPLC, chromatography over silica). All stereoisomers are included within the scope of the disclosure. Where a single enantiomer or diasteromer is disclosed, the disclosure also covers the other enantiomers or diastereomers, and also racemates; in this regard, particular reference is made to the specific compounds listed herein.

Geometric isomers may also exist in the compounds of the present disclosure. The present disclosure contemplates the various geometric isomers and mixtures thereof resulting from the arrangement of substituents around a carbon-carbon double bond and designates such isomers as of the Z or E configuration, wherein the term "Z" represents substituents on the same side of the carbon-carbon double bond and the term "E" represents substituents on opposite sides of the carbon-carbon double bond.

The disclosure therefore includes all variant forms of the defined compounds, for example any tautomer or any pharmaceutically acceptable salt, ester, acid or other variant of the defined compounds and their tautomers as well as substances which, upon administration, are capable of providing directly or indirectly a compound as defined above or providing a species which is capable of existing in equilibrium with such a compound.

Synthesis

The compounds may be synthesised as described in the patent specifications referenced above, e.g. WO 04/103306 and US 2005/0014728.

Administration & Pharmaceutical Formulations

The compounds of the invention will normally be administered orally, intravenously, subcutaneously, buccally, rectally, dermally, nasally, tracheally, bronchially, by any other parenteral route, as an oral or nasal spray or via inhalation, The compounds may be administered in the form of pharmaceutical preparations comprising prodrug or active compound either as a free compound or, for example, a pharmaceutically acceptable non-toxic organic or inorganic acid or base addition salt, in a pharmaceutically acceptable dosage form. Depending upon the disorder and patient to be treated and the route of administration, the compositions may be administered at varying doses.

Typically, therefore, the pharmaceutical compounds of the invention may be administered orally or parenterally ("parenterally" as used herein, refers to modes of administration which include intravenous, intramuscular, intraperitoneal, intrasternal, subcutaneous and intraarticular injection and infusion) to a host. In the case of larger animals, such as humans, the compounds may be administered alone as an alternative to administration as compositions in combination with pharmaceutically acceptable diluents, excipients or carriers.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

In the treatment, prevention, control, amelioration, or alleviation of a symptom of a peripheral neuropathy, an appropriate dosage level will generally be about 0.01 to 500 mg per kg patient body weight per day which can be administered in single or multiple doses. The dosage level may be about 0.1 to about 250 mg/kg per day; e.g. about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0 or 1000.0 milligrams of the active ingredient. The compounds may be administered on a regimen of 1 to 4 times per day, preferably once or twice per day. The dosage regimen may be adjusted to provide the optimal therapeutic response.

According to a further aspect of the invention there is thus provided a pharmaceutical composition including a compound of the disclosure, in admixture with a pharmaceutically acceptable adjuvant, diluent or carrier.

Pharmaceutical compositions of this invention for parenteral injection suitably comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants.

These compositions may also contain adjuvants such as preservative, wetting agents, emulsifying agents and dispersing agents. Prevention of the action of microorganisms may be ensured by the inclusion of various antibacterial and antifungal agents, for example, paraben, chlorobutanol or phenol sorbic acid. It may also be desirable to include isotonic agents such as sugars or sodium chloride, for example. Prolonged absorption of the injectable pharmaceutical form may be brought about by the inclusion of agents (for example aluminum monostearate and gelatin) which delay absorption.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are suitably made by forming microencapsule matrices of the drug in biodegradable polymers, for example polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use.

Solid dosage forms for oral administration include capsules, tablets, pills, powders and granules. In such solid dosage forms, the active compound is typically mixed with at least one inert, pharmaceutically acceptable excipient or carrier such as sodium citrate or dicalcium phosphate and/or one or more: a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycol, for example.

Suitably, oral formulations contain a dissolution aid. The dissolution aid is not limited as to its identity so long as it is pharmaceutically acceptable. Examples include nonionic surface active agents, such as sucrose fatty acid esters, glycerol fatty acid esters, sorbitan fatty acid esters (e.g. sorbitan trioleate), polyethylene glycol, polyoxyethylene hydrogenated castor oil, polyoxyethylene sorbitan fatty acid esters, polyoxyethylene alkyl ethers, methoxypolyoxyethylene alkyl ethers, polyoxyethylene alkylphenyl ethers, polyethylene glycol fatty acid esters, polyoxyethylene alkylamines, polyoxyethylene alkyl thioethers, polyoxyethylene polyoxypropylene copolymers, polyoxyethylene glycerol fatty acid esters, pentaerythritol fatty acid esters, propylene glycol monofatty acid esters, polyoxyethylene propylene glycol monofatty acid esters, polyoxyethylene sorbitol fatty acid esters, fatty acid alkylolamides, and alkylamine oxides; bile acid and salts thereof (e.g. chenodeoxycholic acid, cholic acid, deoxycholic acid, dehydrocholic acid and salts thereof, and glycine or taurine conjugate thereof); ionic surface active agents, such as sodium laurylsulfate, fatty acid soaps, alkylsulfonates, alkylphosphates, ether phosphates, fatty acid salts of basic amino acids; triethanolamine soap, and alkyl quaternary ammonium salts; and amphoteric surface active agents, such as betaines and aminocarboxylic acid salts.

The solid dosage forms of tablets, dragees, capsules, pills, and granules can be prepared with coatings and shells such as enteric coatings and other coatings well known in the pharmaceutical formulating art. They may optionally contain opacifying agents and may also be of a composition such that they release the active ingredient(s) only, or preferentially, in a certain part of the intestinal tract, and/or in delayed fashion. Examples of embedding compositions include polymeric substances and waxes.

The active compounds may also be in micro-encapsulated form, if appropriate, with one or more of the above-mentioned excipients.

The active compounds may be in finely divided form, for example it may be micronised.

Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents. Suspensions, in addition to the active compounds, may contain suspending agents such as ethoxylated isostearyl alcohols, polyoxyethylene sorbitol and sorbitan esters, microcrystalline cellulose, aluminum metahydroxide, bentonite, agar-agar, and tragacanth and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolisable lipid capable of forming liposomes can be used. The present compositions in liposome form can contain, in addition to a compound of the present invention, stabilisers, preservatives, excipients and the like. The preferred lipids are the phospholipids and the phosphatidyl cholines (lecithins), both natural and synthetic. Methods to form liposomes are known in the art, for example, Prescott, Ed., Methods in Cell Biology, Volume XIV, Academic Press, New York, N.Y. (1976), p 33 et seq.

Advantageously, the compounds of the invention may be orally active, have rapid onset of activity and low toxicity.

The compounds of the invention may have the advantage that they are more efficacious, less toxic, longer acting, have a broader range of activity, more potent, produce fewer side effects, more easily absorbed than, or have other useful pharmacological properties over, compounds known in the prior art.

Combination Therapies

Compounds of the invention may be administered in combination with one or more additional therapeutic agents. Accordingly, the invention provides a pharmaceutical composition comprising an additional agent. The invention also provides a product comprising a compound of the invention and an agent; as a combined preparation for simultaneous, separate or sequential use in therapy.

In particular, a composition or product of the invention may further comprise a therapeutic agent selected from, for example, a compound of the disclosure may be administered in combination with an agent useful for treating a peripheral neuropathy, for example a demyelinating peripheral neuropathy; as examples of such second agents may be mentioned an immunosuppresant (e.g., cyclosporin A, cyclosporin G, FK-506, ABT-281, ASM981, rapamycin, 40-O-(2-hydroxy) ethyl-rapamycin, corticosteroids, cyclophosphamide, azathioprine, methotrexate, leflunomide, mizoribine, mycophenolate mofetil, or 15-deoxyspergualine), a steroid (e.g., prednisone or hydrocortisone), an immunoglobulin, or type 1 interferon. The compound of the disclosure and the second agent can be administered simultaneously or consecutively. Where the compound of the disclosure and the second agent are administered simultaneously, they may be formulated into a single composition or in separate compositions.

Use

Compounds of the invention may be useful in the therapy of a variety of peripheral neurapathies, particularly acute or chronic demyelinating neuropathies. The compounds of the disclosure therefore may be useful in the therapy of one or more of Guillain-Barré syndrome (GBS), chronic inflammatory demyelinating polyradiculoneuropathy (CIDP), multifocal motor neuropathy with conduction block (MMN), and paraproteinaemic demyelinating peripheral neuropathy (PDN). In particular, the neuropathy is CIDP. The effectiveness of the compounds may vary between patients.

The term "therapy" includes treatment to alleviate one or more symptoms of a peripheral neuropathy or to delay progression of such a disease e.g. by preventing or slowing demyelination e.g. peripheral demyelination; it also includes treatment to cure such a disease, to put a subject into a functional state and/or maintain a subject in a functional state, or to prolong time to relapse.

The therapeutic use of the compound may include prophylactic use to prevent, control or reduce the severity of a peripheral neuropathy which the subject is at risk of suffering, as well as treatment to control or reduce the severity of existing disease. The compound may be administered before the onset of symptoms; it may be administered after the onset of symptoms. It may be administered to a subject at risk of suffering a peripheral neuropathy.

The treatments for which the compounds may be used may therefore improve, maintain or delay the deterioration of the medical condition and/or comfort of a patient having, suspected of having, or at risk of having, a peripheral neuropathy.

EXAMPLE

The following Examples illustrate the invention.

Example 1

Synthesis of Compound A

1-{4-[1-(4-Cyclohexyl-3-trifluoromethyl-benzyloxy-imino)-ethyl]-2-ethyl-benzyl}-azetidine-3-carboxylic acid (Compound A)

To a suspension of $MnO_2$ (10 eq) in dioxane is added 1-(3-ethyl-4-hydroxymethyl-phenyl)-ethanone O-(4-cyclohexyl-3-trifluoromethyl-benzyl)-oxime (1 eq). The resulting mixture is refluxed for 10 minutes. After filtration and concentration, the residue is dissolved in MeOH and treated with azetidine-3-carboxylic acid (2 eq) and Et3N (1.5 eq). The resulting mixture is heated at 50° C. for 30 minutes. After cooling to room temperature, $NaBH_3CN$ (3 eq) is added in portions. Purification by preparative LCMS results in 1-{4-[1-(4-cyclohexyl-3-trifluoromethyl-benzyloxyimino)-ethyl]-2-ethyl-benzyl}-azetidine-3-carboxylic acid; $^1$H NMR (400 MHz, $CD_3OD$) δ 1.24 (t, 3H), 1.30-1.60 (m, 5H), 1.74-1.92 (m, 5H), 2.28 (s, 3H), 2.79 (q, 2H), 2.92 (m, 1H), 3.68 (m, 1H), 4.32 (m, 4H), 4.51 (s, 2H) 5.22 (s, 2H), 7.38 (d, 1H), 7.50-7.68 (m, 5H). MS: ($ES^+$): 517.3 $(M+1)^+$.

Example 2

Suppressive Effect of Compound A on Experimental Autoimmune Neuritis

Male Lewis rats (8-10 weeks, 180-200 g, Elevage-Janvier, France) were housed under a 12 h light-12 h dark cycle and with free access to food and water. All animal procedures were in accordance with a protocol approved by the local Administration District Official Committee. All efforts were made to minimize the number of animals and their suffering.

EAN Induction

For EAN induction, rats were immunized by subcutaneous injection into both hind footpads with 100 μL of an inoculum containing 100 μg of synthetic neuritogenic P2 57-81 peptide (GeneScript Corporation, Scotch Plains, N.J., USA). The peptide was dissolved in phosphate buffered saline (PBS) (2 mg/mL) and then emulsified with an equal volume of complete Freund's adjuvant (CFA) containing 2 mg/mL *mycobacterium tuberculosis* to get a final concentration of 1 mg/mL.

EAN clinical scores were evaluated every day as follows: 0=normal, 1=reduced tonus of tail, 2=limp tail, impaired righting, 3=absent righting, 4=gait ataxia, 5=mild paresis of the hind limbs, 6=moderate paraparesis, 7=severe paraparesis or paraplegia of the hind limbs, 8=tetraparesis, 9=moribund, and 10=death (Zhang et al., 2009A).

Compound A treatment

Compound A was separately tested at two concentrations of suspension (3 and 10 mg/kg, suspended in 1% carboxymethylcellulose (CMC, Blanose, Hercules-Aqualon, Dusseldorf, Germany)). The compound A suspensions were intragastrically administrated immediately after induction and then once daily until Day 22 (5 rats per group). For control EAN rats, the same volume of 1% CMC in water was given.

Immunohistochemistry

To evaluate inflammatory cell infiltration and pathological changes in the PNS, five compound A-treated rats (at both concentrations) and five control EAN rats from Day 16 were sacrificed. Rats were deeply anaesthetized with ether and perfused intracardially with 4° C., 4% paraformaldehyde in PBS. Left and right sciatic nerves were quickly removed and post-fixed in 4% formaldehyde overnight at 4° C. Sciatic nerves were cut into two equally long segments, embedded in paraffin, serially sectioned (3 μm) and mounted on silan-covered slides.

After dewaxing, cross-sections of sciatic nerves were boiled (in a 600 W microwave oven) for 15 min in citrate buffer (2.1 g sodium citrate/L, pH 6). Endogenous peroxidase was inhibited with 1% $H_2O_2$ in methanol for 15 min. Sections were incubated with 10% normal pig serum (Biochrom, Berlin, Germany) to block non-specific binding of immunoglobulins and then with the following monoclonal antibodies: W3/13 (1:50; Serotec, Oxford, UK) for T lymphocytes, OX22 (1:200; Serotec, Oxford, UK) for B cells, ED1 for activated macrophages (1:100; Serotec, Oxford, UK). Antibody binding to tissue sections was visualized with biotinylated IgG $F(ab)_2$ secondary antibody fragments (rabbit anti-mouse or rabbit anti-goat; 1:400; DAKO, Hamburg, Germany). Subsequently, sections were incubated with a Streptavidin-Avidin-Biotin complex (DAKO, Hamburg, Germany), followed by development with diaminobenzidine (DAB) substrate (Fluka, Neu-Ulm, Germany). Finally, sections were counterstained with Maier's Hemalum.

To evaluate immunostaining data, the percentages of areas of immunoreactivity (IR) to areas of sciatic nerve cross-sections were calculated. Images of sciatic nerve cross-sections were captured under 50× magnification using Nikon Coolscope (Nikon, Dusseldorf, Germany) with fixed parameters. Images were analyzed using MetaMorph Offline 7.1 (Molecular Devices, Toronto, Canada). Areas of IR were selected by colour threshold segmentation and all parameters were fixed for all images. Areas of sciatic nerve cross-sections were manually selected. For each EAN rat, four cross-sections from root and middle levels of both sides were analyzed.

Results were given as arithmetic means of percentages of areas of IR to areas of sciatic nerve cross-sections and standard errors of means (SEM).

The routine Luxol Fast Blue (LFB) staining was applied to show myelin. Histological changes between Compound A and control EAN rats were compared by an established semi-quantitative method. Briefly, four cross-sections from root and middle level of both sides of EAN rats were analyzed. All perivascular areas present in cross-sections were evaluated by two observers unaware of the treatment, and the degree of pathological alteration was graded semiquantitatively on the following scale: 0=normal perivascular area; 1=mild cellular infiltrate adjacent to the vessel; 2=cellular infiltration plus demyelination in immediate proximity to the vessel; and 3=cellular infiltration and demyelination throughout the section. Results were given as mean histological score (Hartung et al., 1988).

Evaluation and Statistical Analysis

The unpaired t-test was performed to compare difference between Compound A and control EAN rats (Graph Pad Prism 4.0 for windows). For all statistical analyses, significance levels were set at p<0.05.

Results

Suppressive Treatment of EAN by Compound A

EAN was induced by subcutaneous injection of neuritogenic synthetic P2 peptide. For suppressive treatment, 1% CMC in water (the control group) or compound A were orally administrated immediately after immunization and then once daily until Day 22. The first neurologic signs (reduced tail tonus) of control EAN rats were observed at Day 9 (mean clinical score: 0.20±0.13). The neurologic severity of EAN increased fast in the control group with a maximal score at Day 13 (mean neurologic score: 4.80±0.51). Thereafter, the severity of EAN slowly decreased and rats fully recovered by Day 22 (mean clinical scores: 0±0). In compound A-treated EAN rats, greatly reduced neurological signs were seen at Day 14, with maximal scores at Day 15 and full recovery of rats was seen by Day 19. Therefore, compound A treatment almost prevented the development of clinical signs of EAN, dramatically delayed its onset, decreased neurologic severity and shortened duration of EAN very effectively relative to the water/cmc vehicle (FIGS. 1A and 1B).

A further feature of EAN is progressive weight loss after onset of disease. In control and Compound A-treated EAN rats, a slow and continuous weight gain was observed until onset of EAN (Day 9). Thereafter, control EAN rats showed significant weight loss during the period of neurologic disease from Day 10 to 18 post immunization, followed by weight gain during the recovery period (FIG. 2A). In contrast, a reduced level of weight loss was observed in the lower compound A suspension from Day 11 to 16 in EAN rats treated by compound A at the peak of disease onset, again indicating a much less severe course. This effect was more pronounced in the higher dosage suspension, with a small weight loss between days 11 and 12, followed by weight gain (FIG. 2B).

Effects of Suppressive Compound A Treatment on Histopathological Changes in EAN Sciatic Nerves Infiltration of different types of inflammatory cells in sciatic nerves of control or Compound A-treated EAN rats at Day 16 (n=5) was analyzed by immunohistochemistry. Infiltration of T cells (W3/13+), B cells (OX22+) and macrophages (ED1+) was seen in sciatic nerves of control EAN rats. The predominant infiltrating cells were macrophages, whose areas of IR occupied about 2% of the total areas of sciatic nerve on cross-sections. These results are shown in Table 1 below.

TABLE 1

| Test compound | Area of immunoreactivity/area of sciatic nerves (%) for Macrophages (ED1+) | Area of immunoreactivity/area of sciatic nerves (%) for T cells (W3/13+) | Area of immunoreactivity/area of sciatic nerves (%) for B cells (OX22+) |
|---|---|---|---|
| Water vehicle | 2.1 | 0.6 | 0.25 |
| CMC vehicle | 2.2 | 0.56 | 0.91 |
| Compound A (3 mg/kg) | 0.20 | 0.08 | 0.025 |
| Compound A (10 mg/kg) | 0.11 | 0.04 | 0.021 |

In sciatic nerves of EAN rats, compound A significantly suppressed infiltration of T cell, B cells and macrophages.

In sciatic nerves, the mean histological scores measured by LFB staining were markedly lower in Compound A-treated EAN rats. These results are shown in Table 2 below.

TABLE 2

| Test composition | Mean Histological Score |
|---|---|
| Water vehicle | 1.78 |
| CMC vehicle | 1.75 |
| Compound A (3 mg/kg) | 0.51 |
| Compound A (10 mg/kg) | 0.25 |

These results demonstrate that suppressive treatment with Compound A almost prevented EAN and inhibited paraparesis through substantial reduction of infiltration of lymphocytes and macrophages into the peripheral nerves along with decreased local demyelination.

The invention claimed is:

1. A method of treating a subject having a demyelinating peripheral neuropathy selected from chronic inflammatory demyelinating polyradiculoneuropathy, multifocal motor neuropathy with conduction block or paraproteinaemic demyelinating peripheral neuropathy comprising administering to the subject an effective amount of 1-{4-[1-(4-Cyclohexyl-3-trifluoromethyl-benzyloxyimino)-ethyl]-2-ethyl-benzyl}-azetidine-3-carboxylic acid:

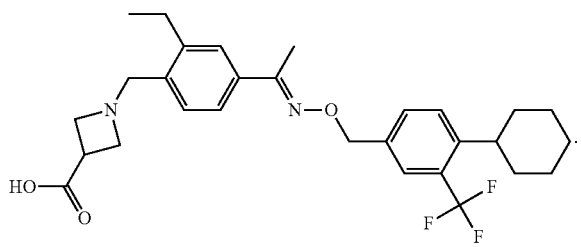 [SMILES: CCc1cc(/C(C)=N/OCc2ccc(C3CCCCC3)c(C(F)(F)F)c2)ccc1CN1CC(C(=O)O)C1]

2. A method of alleviating a symptom of, delaying the progression of, or prolonging time to relapse of a demyelinating peripheral neuropathy selected from chronic inflammatory demyelinating polyradiculoneuropathy, multifocal motor neuropathy with conduction block or paraproteinaemic demyelinating peripheral neuropathy comprising administering to the subject an effective amount of 1-{4-[1-(4-Cyclohexyl-3-trifluoromethyl-benzyloxyimino)-ethyl]-2-ethyl-benzyl}-azetidine-3-carboxylic acid:

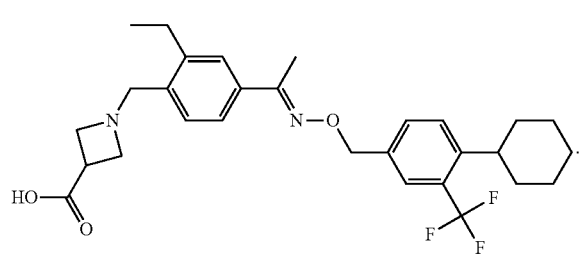 [SMILES: CCc1cc(/C(C)=N/OCc2ccc(C3CCCCC3)c(C(F)(F)F)c2)ccc1CN1CC(C(=O)O)C1]

3. A method of improving or maintaining, or delaying the deterioration of a symptom associated with a subject having a demyelinating peripheral neuropathy selected from chronic inflammatory demyelinating polyradiculoneuropathy, multifocal motor neuropathy with conduction block or paraproteinaemic demyelinating peripheral neuropathy comprising administering to the subject an effective amount of 1-{4-[1-(4-Cyclohexyl-3-trifluoromethyl-benzyloxyimino)-ethyl]-2-ethyl-benzyl}-azetidine-3-carboxylic acid:

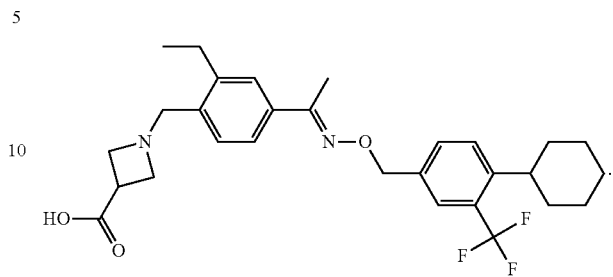

* * * * *